United States Patent

Johanson et al.

Patent Number: 5,289,728
Date of Patent: Mar. 1, 1994

[54] FLOW-NO-FLOW TESTER

[75] Inventors: Jerry R. Johanson, San Luis Obispo; Kerry D. Johanson, Atascadero; Brian D. Cox, San Luis Obispo, all of Calif.

[73] Assignee: JR Johanson, Inc., San Luis Obispo, Calif.

[21] Appl. No.: 781,018

[22] Filed: Oct. 16, 1991

Related U.S. Application Data

[63] Continuation-in-part of Ser. No. 610,530, Nov. 8, 1990, Pat. No. 5,117,699.

[51] Int. Cl.⁵ .................................. G01N 11/00
[52] U.S. Cl. .................................... 73/866
[58] Field of Search .......... 73/38, 863, 864.16–864.18, 73/864.62, 866, 818, 821, 823, 825, 54.11–54.14, 864.01

[56] References Cited

U.S. PATENT DOCUMENTS

| | | | |
|---|---|---|---|
| 2,633,027 | 3/1953 | Bunnell | 73/866 |
| 2,743,605 | 5/1956 | Gamlen | 73/54.11 |
| 2,880,609 | 4/1959 | Byrkett et al. | 73/38 |
| 3,054,286 | 9/1962 | Karol | 73/825 |
| 3,985,032 | 10/1976 | Avakian | 73/864.01 |
| 4,316,383 | 2/1982 | Fruman et al. | 73/54.12 |
| 4,615,210 | 10/1986 | Wright | 73/54.11 |
| 4,679,441 | 7/1987 | Johnson et al. | 73/825 |
| 4,719,809 | 1/1988 | Johansson et al. | 73/866 |
| 5,058,674 | 10/1991 | Schultz et al. | 73/864.62 |
| 5,117,699 | 6/1992 | Johanson et al. | 73/866 |

FOREIGN PATENT DOCUMENTS

| | | | |
|---|---|---|---|
| 1276369 | 8/1968 | Fed. Rep. of Germany | 73/864.16 |
| 1017969 | 5/1983 | U.S.S.R. | 73/866 |
| 1449907 | 1/1989 | U.S.S.R. | 73/866 |

Primary Examiner—Robert Raevis
Attorney, Agent, or Firm—Daniel C. McKown

[57] ABSTRACT

An instrument for measuring certain physical properties of a sample of particulate material so that the flow characteristics of the material can be determined includes an improved compaction assembly having an upper piston that is surrounded by a retractable sleeve and further includes an improved test cell having cylindrical walls, having a failure outlet smaller than the diameter of the failure piston, and having a false bottom that can easily be removed from beneath a sample of compacted material to permit the failure portion of the test to be carried out. The tester can be used for determining the confined yield strength of the material, its bulk density, and its permeability.

6 Claims, 4 Drawing Sheets

FLOW-NO-FLOW TESTER

BACKGROUND OF THE INVENTION

1. Reference to Earlier Applications

The present application is a continution-in-part of copending U.S. patent application Ser. No. 07/610,530, filed Nov. 8, 1990 for IMPROVED FLOW-NO-FLOW TESTER, now U.S. Pat. No. 5,117,699 issued Jun. 2, 1992, and the priority of that application is claimed for subject matter common to that application and the present application.

2. Field of the Invention

The present invention is in the field of bulk particulate solids, and more specifically relates to a testing apparatus and method for determining on the basis of bench-scale testing whether particulate material will flow under the action of gravity through an outlet in the bottom of a container, such as a hopper.

3. The Prior Art

Bulk solids in a divided state such as flour, sugar, ores, powders, dry chemicals, and coal are generally stored in silos that include a hopper at the lower end of the silo through which the bulk solids are to be discharged under the action of gravity. One of the problems of designing such containers is sizing the outlet so that the solids do not form an obstruction by arching across the outlet. The size of the outlet required to prevent arching depends on the physical properties of the bulk solids, specifically, the unconfined yield strength of the material, and the density of the material. The steepness of the walls of the hopper must also be considered.

The present invention is an outgrowth and improvement upon the apparatus shown and described in U.S. Pat. No. 4,719,809, issued Jan. 19, 1988 to Jerry R. Johanson and Kerry D. Johanson. The contents of that patent are hereby incorporated by reference into the present discussion as if reproduced herein verbatim. The patent is believed to be the most relevant prior art in relation to the present invention.

FIG. 1 is adapted from the aforementioned patent and shows a test apparatus described therein. The apparatus includes a mold ring 24' that rests upon a test cell 12'. The test cell 12' includes an inwardly-facing conical surface 14' and the test cell 12' is closed at its lower end by a conical surface 18'. The test cell is filled with a particulate material 32', which is compressed by a weighted disk 26'. After the material 32' has compacted, the mold ring 24' is removed and the material is scraped off even with the top of the test cell 12'.

Next, the entire filled test cell 12' is inverted and a failure load is applied downwardly to the plug 10'. As the failure load is gradually increased, a point is reached at which the material suddenly fails and falls out of the test cell. As discussed at greater length in the aforementioned U.S. Pat. No. 4,719,809, the size of outlet required to prevent arching can be calculated from the compaction load, the failure load, the density of the material, and the shape and dimensions of the outlet. That patent hints, at column 8, lines 21-28, that it might not be necessary to invert the test cell after the consolidation phase, but no apparatus is shown or described for bringing about this result.

In U.S. Pat. No. 3,890,830 issued Jun. 24, 1975 to Dyck, there is shown an apparatus for determining the compressibility and/or moisture content of particulate materials. Although there is a superficial resemblance to the apparatus of the present invention, upon closer study it will be seen that both the apparatus and the method of Dyck's tester are basically different from that of the present invention.

In U.S. Pat. No. 2,633,027 issued Mar. 31, 1953 to Bunnell, there is shown an apparatus and method for testing the flow characteristics of granular materials. The apparatus includes a cylindrical chamber which can selectively be opened and closed at its lower end, and a piston at its upper end for exerting compressive forces on the material. As will be seen below, both the structure and the operation of this apparatus differs from that of the present invention.

SUMMARY OF THE INVENTION

It is an objective of the present invention to provide an improved flow-no-flow tester that is easier to use, compared with previous testers, and that yields more accurate results.

In using the tester described in U.S. Pat. No. 4,719,809 referred to above, it sometimes happened that when the test cell was inverted for application of the failure load, the compacted particulate material collapsed and fell out of the test cell before the test cell could be brought to its final position. Because of the evident nature of the problem, the accuracy of the results was not effected, but the test had to be repeated at some loss of time. The present invention solves this problem by eliminating the need to invert the test cell.

Less apparent, but nonetheless important is the improvement in the accuracy that is obtained with the apparatus of the present invention. In the apparatus of U.S. Pat. No. 4,719,809, the test cell is tapered. This has been found to cause a non-uniform compaction of the solids, especially in the tapered areas, which was compensated for by use of a domed top; however, the degree of compaction depended on the properties of the material being tested. In the present invention, the compaction takes place in a cylindrical mold with parallel top and bottom surfaces. This greatly improves the uniformity of compaction. In addition the present invention compacts the solids across the entire cell diameter including at the outer diameter of the cell and thus more accurately measures the compaction pressure.

These improvements are made possible through the use, in the present invention, of a two part compaction unit that includes a hollow cylindrical sleeve that surrounds an upper piston and is flush with one end of it. The upper piston is attached to a load cell for measuring an applied force. During compaction, both the hollow cylindrical sleeve and the upper piston move downward together into a cylindrical test cell providing a uniform compaction across the entire area of the test cell. The cylindrical sleeve is susceptible to frictional forces from the test cell wall, but the upper piston moving in concert with the outer cylinder is not subject to frictional forces and consequently accurately registers the applied compaction force on the load cell to which it is connected. When the tester is used to measure the yield strength of the compacted solid, the cylindrical sleeve is raised relative to the upper piston and the upper piston is used to apply the failure force. This relative upward movement of the cylindrical sleeve also facilitates cleaning of any granular solids that might have entered the small gap between the top piston and the outer cylinder.

The cylindrical design of the test cell of the present invention allows for the vertical displacement of the compaction assembly without any possibility of impinging on the walls of the test chamber, which were tapered in the previous invention. This allows compaction in the same vertical direction as failure. This eliminates any need to invert the test cell as was required in the previous invention. The test sample is supported by a lower piston during compaction. When the test cell is used for measuring the solids strength, the lower piston is lowered and the test sample is failed by the upper piston. Prior to failure the hollow cylindrical sleeve is moved upward with respect to the upper piston so as to prevent it from interfering with the failure process. The upper piston is sized somewhat smaller than the failure outlet. This prevents pinching of solids between the top piston and the failure outlet.

The novel features which are believed to be characteristic of the invention, both as to organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

DETAILED DESCRIPTION OF THE PREFERRED EMBODIMENT

Figure 2:
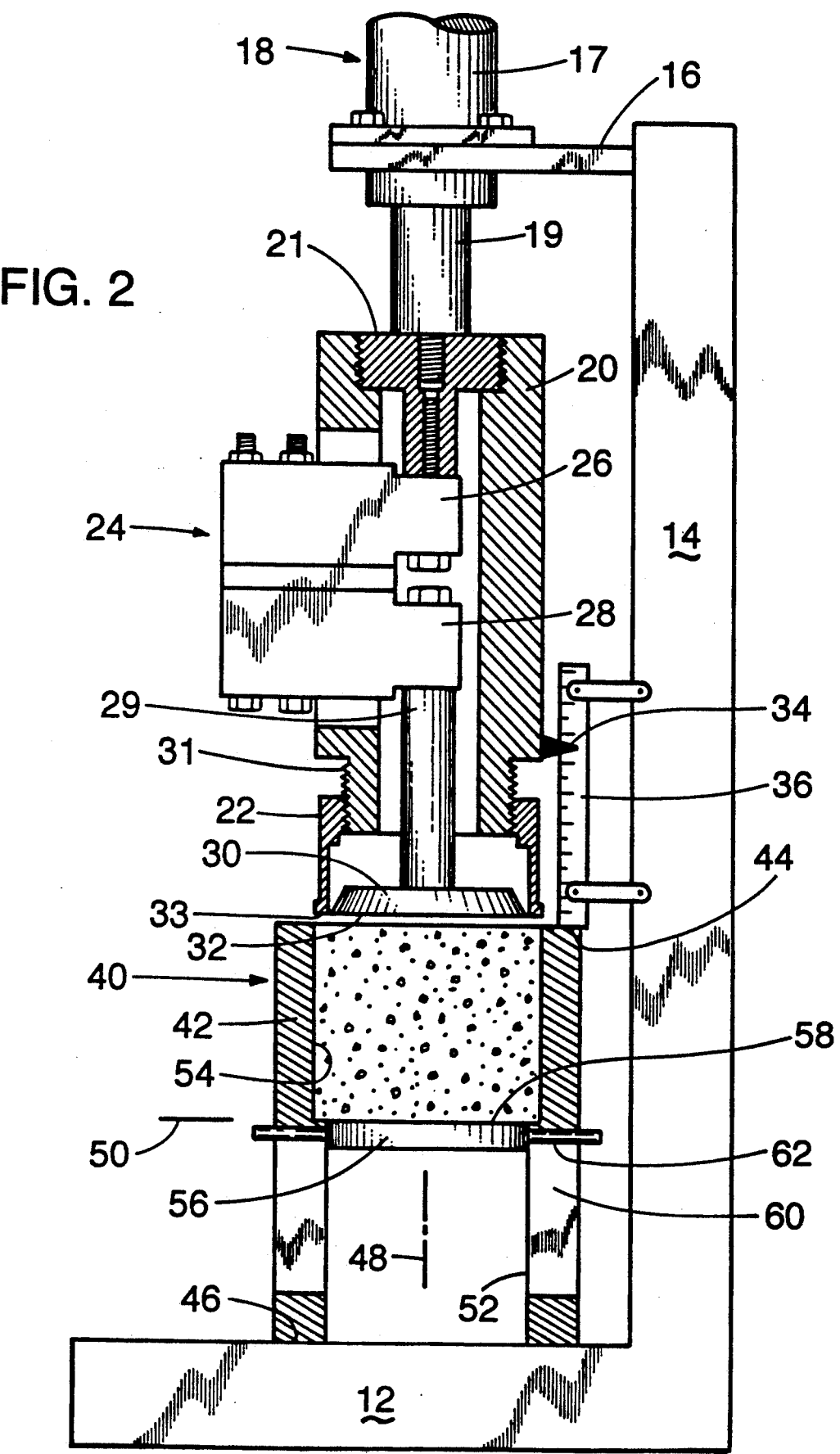
FIG. 2 is a side elevational view partly in cross section showing a preferred embodiment of the flow-no-flow tester of the present invention.

The preferred embodiment of the flow-no-flow tester of the present invention is shown in FIG. 2. A column 14 extends vertically upward from a base 12, and supports an arm 16 above the base but spaced from it. The arm 16 supports a stationary portion 17 of a linear actuator 18, with the movable ram portion 19 directed downwardly so as to be able to exert a downward thrust on the items to be described.

A hollow cylindrical body 20 transmits the downward thrust of the ram portion 19 of the linear actuator to the cylindrical sleeve 22. Some of the thrust is transmitted through the plug 21 to the upper side 26 of the load cell 24, which in turn transmits the thrust from its lower side 28 through the column 29 to the upper piston 30.

The inside diameter of the cylindrical sleeve 22 is slightly larger than the diameter of the upper piston 30 so that the upper piston 30 never touches the cylindrical sleeve 22. Also, the load cell 24 does not touch the hollow cylindrical body 20. Therefore, the load cell measures only the force applied to the upper piston 30. The threads 31 at the lower end of the hollow cylindrical body 20 permit axial adjustment of the cylindrical sleeve 22 with respect to the upper piston 30.

In particular, the lower end 33 of the cylindrical sleeve 22 can be made to be coplanar with the downwardly-facing planar face 32 of the upper piston 30. By rotation of the cylindrical sleeve 22, its lower end 33 can be retracted upwardly with respect to the downwardly-facing planar face 32 of the upper piston 30. These two positions of the cylindrical sleeve 22 with respect to the upper piston 30 are seen in FIGS. 3 and 4, respectively.

Figure 3:
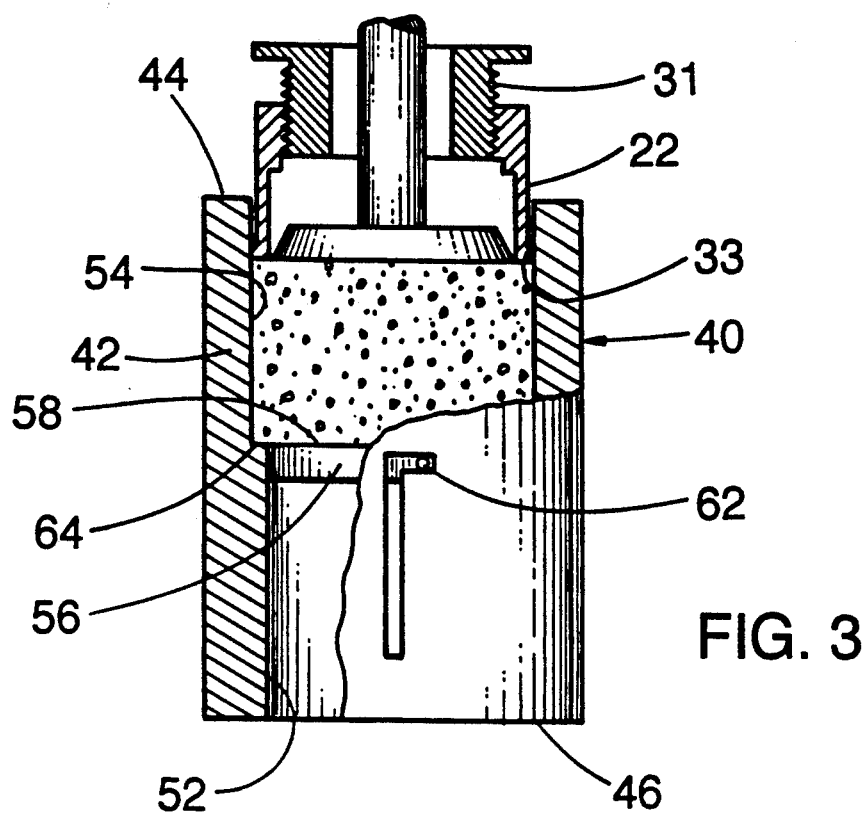
FIG. 3 is a fractional side elevational view in cross section showing the test cell of the preferred embodiment in the compaction mode.
Figure 4:
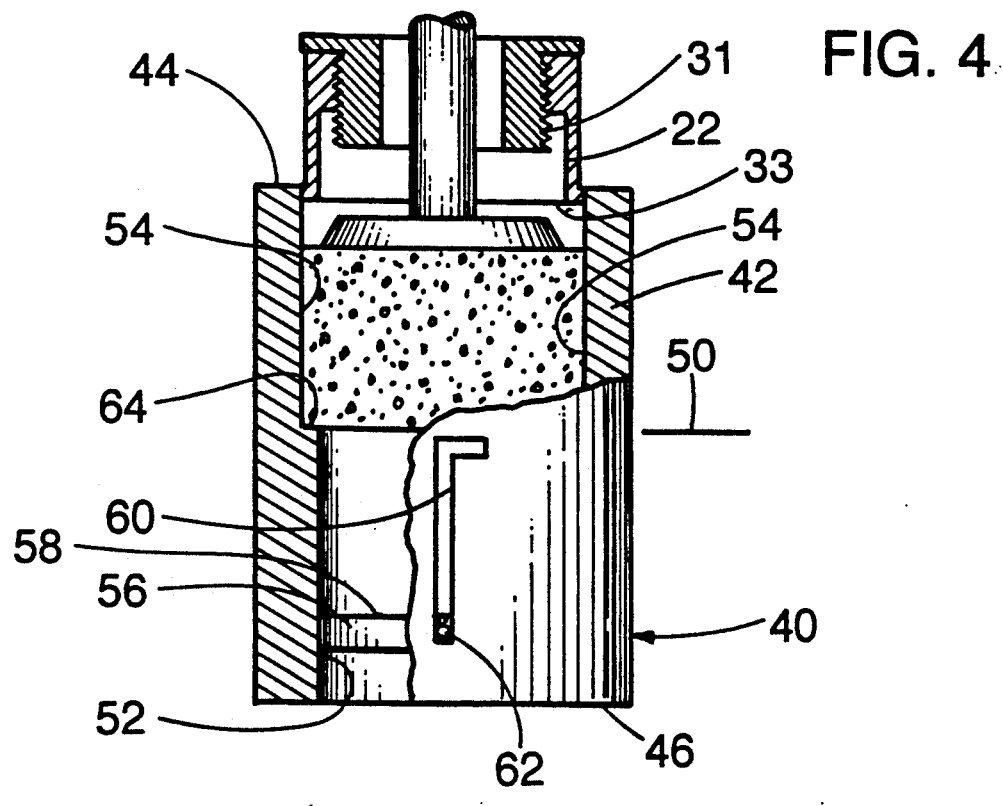
FIG. 4 is a fractional side elevational view in cross section showing the test cell of the preferred embodiment in the failure mode.

FIGS. 3 and 4 show a removable test cell used in the preferred embodiment of the flow-no-flow tester of the present invention. The test cell 40 includes a unitary hollow body 42 having an upper end 44 and a lower end 46. In the preferred embodiment, the test cell has a cylindrical shape and is symmetric about a vertical axis 48.

A lower bore 52 extends vertically upward from the lower end 46 of the hollow body 42 to an imaginary horizontal medial plane 50. Likewise, an upper bore 54 extends downwardly into the hollow body 42 from its upper end 44 to the imaginary horizontal medial plane 50.

The unitary hollow body 42 further includes a slot 60 in which the pin 62 rides to permit the lower piston 56 to be moved from the upper position shown in FIGS. 2 and 3 to the lower position shown in FIG. 4. In the upper position shown in FIGS. 2 and 3, the upwardly facing planar face 58 of the lower piston 56 lies in the imaginary horizontal medial plane 50, but in the lower position shown in FIG. 4, the upwardly-facing planar face 58 lies between the imaginary horizontal medial plane 50 and the lower end 46 of the body 42.

Figure 7:
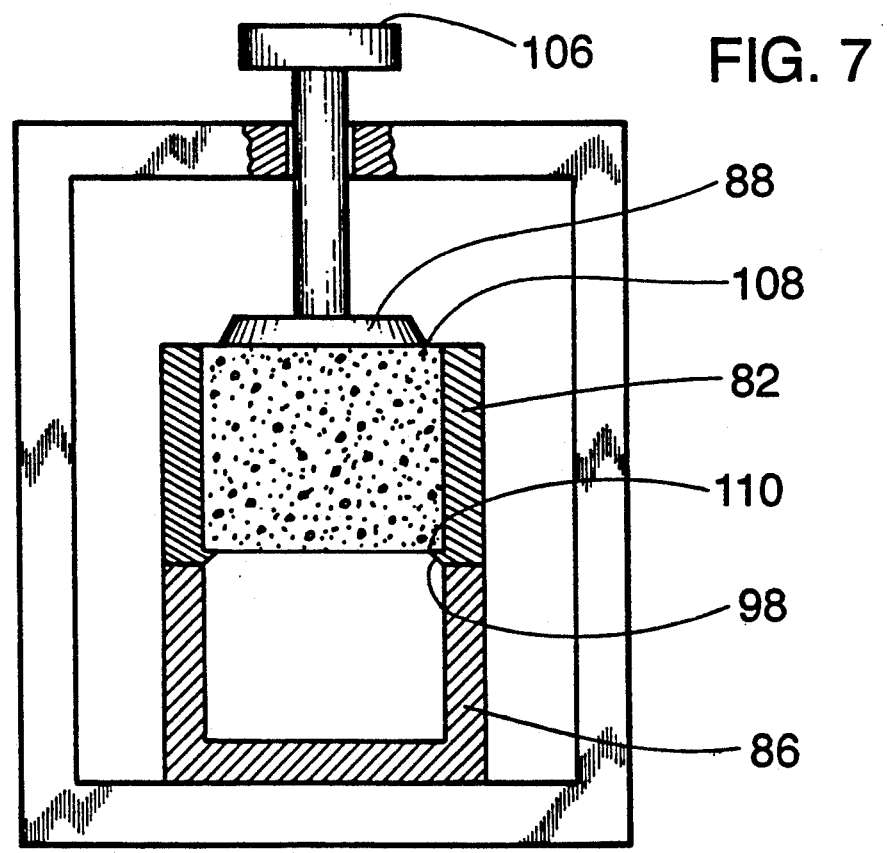
FIG. 7 is an elevational view in cross section showing the alternative embodiment of FIG. 6 in the failure mode.

Because of the difference in the diameters of the upper bore 54 and the lower bore 52, a small ledge 64 is formed within the hollow body 42, and in the preferred embodiment the width of this ledge is large enough so that the failure surface of the solids always lies within the solids and does not propagate to the wall of the upper bore 54. As illustrated in FIG. 7, in an embodiment intended for use with solids that are springy, the area below the failure area must taper outwardly to insure that when the springy solids expand upon failure, they are not restrained by the portion of the lower bore 52 below the ledge 64.

In normal operation of the flow-no-flow tester shown in FIGS. 2, 3 and 4, initially, the test cell 40 is removed from beneath the upper piston 30, and the lower piston 56 is set to its upper position. Thereafter, the particulate material to be tested is placed in the upper bore 54 of the test cell 40. Any portion of the material that extends above the upper end 44 is scraped off, and then the test cell is returned to its normal position immediately below the upper piston 30.

Next, the position of the cylindrical sleeve 22 is adjusted with respect to the downwardly-facing planar face 32 of the upper piston 30 so as to bring the lower end 33 of the cylindrical sleeve into the plane of the face 32.

Thereafter, a compaction load is applied by the linear actuator 18 to compact the particulate material in the test cell. FIG. 3 shows the configuration of the apparatus after the compaction has taken place. Because the upper piston 30 does not contact the lower end 33 of the cylindrical sleeve 22, the force measured by the load cell is unaffected by friction and very accurately relates to the actual force applied by the upper piston, from which the true applied compacting pressure can be calculated.

When the compaction phase has been completed, the cylindrical sleeve 22 is retracted from its previous position with respect to the upper piston 30, as best seen by comparing FIG. 3 with FIG. 4. Also, after the compaction phase has been completed, the lower piston 56 is brought to the position shown in FIG. 4 by manual rotation and lowering of the pin 62 within the slot 60. FIG. 4 shows the configuration of the apparatus in the failure mode. With respect to FIG. 4, it should be noted that because the diameter of the upper piston 30 is less than the diameter of the upper bore 54, so that friction between these elements is completely eliminated and also the effect of frictional forces between the compacted material and the upper bore of the test cell is eliminated. Further, as mentioned above, the ledge 64 serves to prevent the failure surface from contacting the wall of the test cell, and this further increases the accuracy of the measurement of the failure load. With the apparatus in the configuration of FIG. 4, as the pressure exerted by the upper piston 30 is gradually increased, a point is reached at which the compacted material fails and falls into the lower portion of the test cell. The force measured at the instant of failure is the failure load.

In the preferred embodiment, a graduated scale 36 is removably mounted on the upper end 44 of the test cell and a pointer 34 affixed to the hollow cylindrical body 20 are provided for use in measuring the depth of the compacted solids.

The confined yield strength of a particulate solid can be measured using the tester of the preferred embodiment shown in FIGS. 2, 3 and 4 by: placing a weighed quantity of solids into the test cell; leveling the top surface; applying a compaction load to a predetermined volume; measuring the height of the solids in the test cell; calculating the solids bulk density from the known cell volume; removing the compaction load; lowering the bottom piston; applying a load to the failure piston; and, measuring the failure load FL. The unconfined yield strength $f_c$ is then calculated as two times the maximum failure sheer stress. The strength is approximated by:

$$f_c = 2(YAH + FL)/(PH)$$

where:
Y is the solids bulk density
A is the area of the failure opening
H is the height of the sample in the cell at failure
FL is the failure load
P is the perimeter of the failure opening.

This approximate formula is arrived at by assuming that the compacted solids in the test cell has a uniform strength and that the solids during failure (when the lower piston is removed) is unconfined. During failure, the maximum sheer stress occurs approximately along an approximately cylindrical surface connecting the upper piston and the lower bore 52.

The same apparatus can be used to measure the bulk density of the particulate solids under a given consolidation pressure. This is accomplished by weighing the solids in the test cell and measuring the position of the compaction (upper) piston 30 with respect to the lower piston 56. This position is used to determine the compacted volume of the solids. The bulk density is then determined by the weight of the solids divided by the measured volume.

Figure 5:
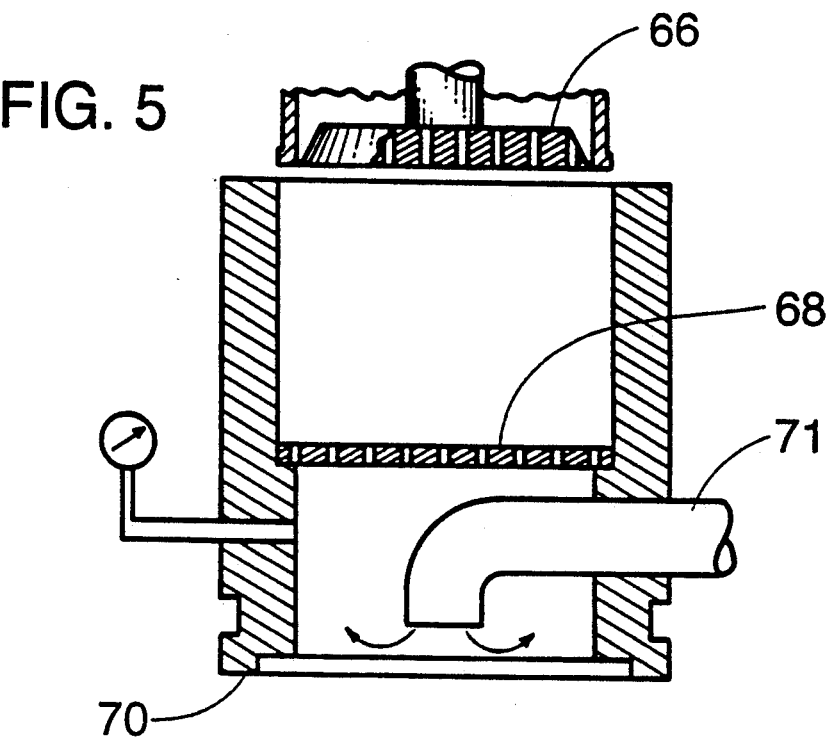
FIG. 5 is a fractional side elevational view in cross section showing a test cell used in an alternative embodiment for measuring permeability.
Figure 1:
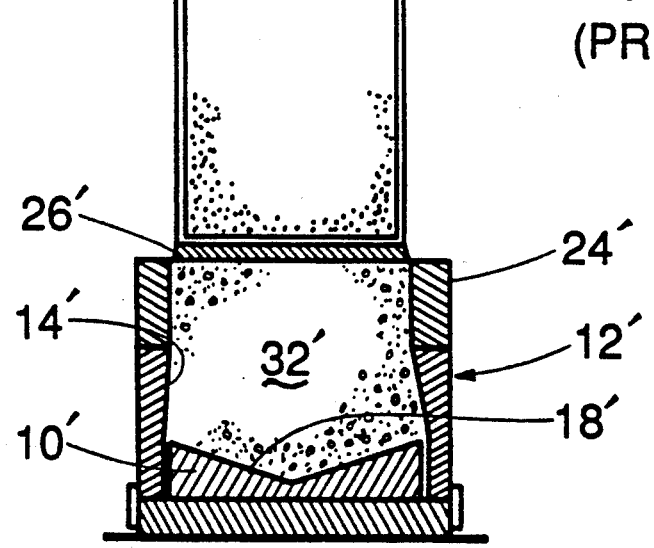
FIG. 1 is a side elevational view partly in cross section showing a tester of the prior art.

With only a slight modification, the test apparatus of FIGS. 2-4 can also be used to measure the permeability of solids. In this case, the upper piston 30 and the lower piston 56 are replaced by perforated pistons 66, 68 respectively, through which air may freely pass, as shown in FIG. 5. The lower perforated piston 68 does not need to be removable in this case, although it may be removable. Air is introduced at a measured rate through the duct 71 into the test cell below the perforated lower piston 68 and forced to flow up through the particulate solids by sealing the lower end 70 of the test chamber. The air pressure and air flow rate are measured, and the permeability of the solids is determined.

The preferred embodiment shown in FIGS. 2, 3 and 4 uses a linear actuator 18 to provide the compaction and failure forces. In an alternative embodiment shown in FIGS. 6 and 7, gravity is used to apply these loads.

Figure 6:
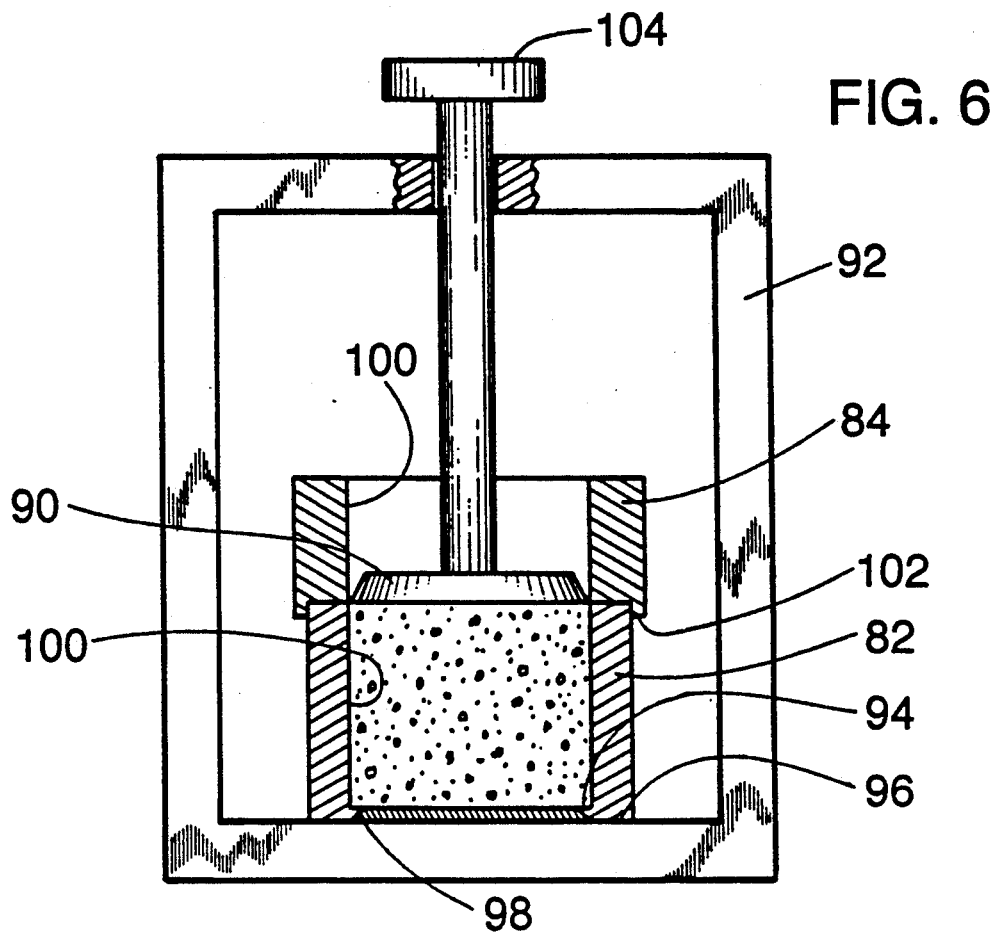
FIG. 6 is a side elevational view in cross section showing an alternative embodiment of the flow-no-flow tester of the present invention in the compaction mode.

In the alternative embodiment of FIGS. 6 and 7, the test cell is a modification of the test cell used in the preferred embodiment of FIGS. 1-4, and this modified test cell 82 is assisted by the removable mold ring 84 of FIG. 6 and by the failure base 86 of FIG. 7. It is also necessary in accordance with the alternative embodiment to employ a failure piston 88 whose diameter is appreciably less than the inside diameter of the test cell 82 and which also is smaller than the compaction piston 90 of FIG. 6. A support frame 92 serves to guide the compaction piston and the failure piston in a vertical direction and also serves to center the test cell directly beneath the pistons.

In accordance with the alterntive embodiment, the test cell 82 consists of a hollow cylindrical unitary body having an inwardly directed ledge 94 near its bottom 96. The underside 98 of the ledge tapers downwardly and outwardly to provide relief for the failure of springy solids such as rubber particles. The compaction piston 90 of FIG. 6 fits into the bore 100 of the test cell in a loose sliding fit. The removable mold ring 84 includes an axially extending lip 102 that serves to align the mold ring with the test cell. The compaction load is placed manually on the load platform 104.

The user of the apparatus of FIG. 6 must include sufficient material within the test cell and removable mold ring so that after compaction has taken place, the test cell will be filled to its entire height. After compaction, the mold ring 84 is lifted from the test cell 82 to insure that all of the compaction force rests on the solids and is not dissipated in friction between the mold ring 84 and the piston 90. Thereafter, the piston 90 is raised manually and replaced by the failure piston 88. The failure base 86 is then placed under the test cell 82, and a failure load is then applied to the failure load platform 106 of FIG. 7 until the material fails and falls into the failure base 86. As in the preferred embodiment of FIGS. 2-4, the failure surface extends approximately from the outer edge 108 of the failure piston to the inner edge 110 of the ledge 94, and therefore does not touch the test cell wall 100.

The flow-no-flow tester of the alternative embodiment of FIGS. 6 and 7 can be used to perform all of the tests that can be performed by use of the preferred embodiment of FIGS. 2-4.

Thus, there has been described an improved flow-no-flow tester which in a preferred embodiment includes a novel compacting assembly that includes a piston surrounded by a retractable cylindrical sleeve, and which further employs a novel test cell having a false bottom that can be removed from beneath the compacted material to permit the material to fall into a lower compartment during failure. In the preferred embodiment, the compaction load is applied by a linear actuator and is measured by a load cell.

In an alternative embodiment, gravity is used to produce the compaction and failure loads which are applied to compaction and failure pistons, respectively. In the alternative embodiment, a removable mold ring facilitates compaction of the material into a test cell that has an inwardly directed ledge at its lower end. After the material has been compacted in the test cell, the test cell is placed on top of a failure base that provides an empty hollow chamber into which the material can fall as it fails under a failure load that is applied to the failure piston. The diameter of the failure piston is smaller than the clear diameter of the failure outlet at the bottom of the test cell, so as to prevent the failure surface from contacting the wall of the test chamber, thereby increasing the accuracy of the tester.

The improved flow-no-flow tester of the present invention is useful in those industries in which particulate materials are stored and moved. The tester enables its user to determine certain pertinent physical properties of the material which bear on its ability to flow from a storage container. These physical properties include: the confined yield strength, the permeability of the material, and its bulk density.

The foregoing detailed description is illustrative of several embodiments of the invention, and it is to be understood that additional embodiments thereof will be obvious to those skilled in the art. The embodiments described herein together with those additional embodiments are considered to be within the scope of the invention.

What is claimed is:

1. A flow-no-flow tester comprising in combination: a test cell including a hollow body having an upper end and a lower end, having an upper bore extending downwardly along a vertical axis from the upper end to an imaginary horizontal plane located above the lower end, said hollow body further including surfaces defining an undercut ledge having an upper surface lying in the imaginary horizontal plane and projecting radially inwardly from the upper bore, to a failure outlet, and having a lower surface extending from the failure outlet downwardly and radially outwardly to the lower end of said hollow body;
   a failure piston having a diameter less than the diameter of said failure outlet; and,
   guide means associated with said failure piston for restraining its motion to a vertical direction and for maintaining the center of said failure piston on the axis of said bore.

2. A flow-no-flow tester comprising:
   a hollow body having an upper end and a lower end, having an upper bore extending downwardly along a vertical axis from the upper end to an imaginary horizontal plane located above the lower end, said hollow body further including surfaces defining an undercut ledge having an upper surface lying in the imaginary horizontal plane and projecting radially inwardly from the upper bore to a failure outlet, and having a lower surface extending from the failure outlet downwardly and radially outwardly to the lower end of said hollow body; and,
   a failure piston having a diameter less than the diameter of the failure outlet.

3. A flow-no-flow tester comprising:
   a hollow body having an upper end and a lower end, having an upper bore extending downwardly along a vertical axis from the upper end to an imaginary horizontal plane located above the lower end, said hollow body further including surfaces defining an undercut ledge having an upper surface lying in the imaginary horizontal plane and projecting radially inwardly from the upper bore to a failure outlet, and having a lower surface extending from the failure outlet downwardly and radially outwardly to the lower end of said hollow body;
   a compaction piston sized to fit into the upper bore in a loose sliding fit when a material is to be compacted, said compaction piston including an outer sleeve that fits into the upper bore in a loose sliding fit and further including an upper piston that fits closely within the outer sleeve without touching it;
   means for measuring an axial load applied to the upper piston; and
   removable support means lying below the imaginary horizontal plane and closing the failure outlet to temporarily prevent the material being compacted from being pushed through the failure outlet.

4. The flow-no-flow tester of claim 3 further comprising means for altering the axial position of the outer sleeve with respect to the upper piston.

5. A flow-no-flow tester comprising in combination:
   a base;
   a column extending upward from said base;
   an arm extending horizontally from said column over said base at some distance from said base;
   a linear actuator supported by said arm for thrusting downwardly from said arm;
   a hollow cylindrical body oriented with its axis vertical, and having an upper end in contact with said linear actuator;
   a cylindrical sleeve coaxial with said hollow cylindrical body and having a lower end lying in a horizontal plane;
   a load cell located below said linear actuator and having an upper side and a lower side, for measuring a compressive force urging together the upper side and the lower side;
   first means connecting said linear actuator to the upper side of said load cell;
   an upper piston having a downwardly-facing planar face;
   second means extending upward from said upper piston within said hollow cylindrical body and connecting said upper piston to the lower side of said load cell;
   adjustment means coupling said cylindrical sleeve to said hollow cylindrical body for altering the position of said cylindrical sleeve vertically with respect to said hollow cylindrical body from a first position in which the lower end of said cylindrical sleeve is coplanar with the downwardly-facing planar face of said upper piston to a second position in which the lower end of said cylindrical sleeve is higher than the downwardly-facing planar face of said upper piston;

the inside diameter of said cylindrical sleeve being slightly larger than the diameter of said upper piston so that said upper piston never touches said cylindrical sleeve;

whereby, a downward force exerted by said linear actuator is applied to both said cylindrical sleeve and to said upper piston, but only the force applied to the upper piston is measured by said load cell.

6. The flow-no-flow tester of claim 5 wherein said upper piston further includes portions defining passages through it.

* * * * *